(12) United States Patent
Kratz et al.

(10) Patent No.: US 12,126,389 B2
(45) Date of Patent: *Oct. 22, 2024

(54) SYSTEM FOR GENERATING ACCURATE REFERENCE SIGNALS FOR TIME-OF-ARRIVAL BASED TIME SYNCHRONIZATION

(71) Applicant: ZaiNar, Inc., Redwood City, CA (US)

(72) Inventors: Philip Kratz, Redwood City, CA (US); Mainak Chowdhury, Redwood City, CA (US)

(73) Assignee: ZaiNar, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/879,740

(22) Filed: Aug. 2, 2022

(65) Prior Publication Data

US 2023/0023803 A1     Jan. 26, 2023

Related U.S. Application Data

(63) Continuation of application No. 17/129,682, filed on Dec. 21, 2020, now Pat. No. 11,444,703, which is a
(Continued)

(51) Int. Cl.
*H04B 17/10* (2015.01)
*C07C 41/01* (2006.01)
(Continued)

(52) U.S. Cl.
CPC ........... *H04B 17/104* (2015.01); *C07C 41/01* (2013.01); *C07G 1/00* (2013.01); *C08B 37/0057* (2013.01);
(Continued)

(58) Field of Classification Search
CPC ........ H04B 17/104; H04B 17/14; H04B 1/16; H04B 1/40; H04L 5/0048; H04L 7/0079
See application file for complete search history.

(56) References Cited

U.S. PATENT DOCUMENTS

10,291,384 B2 *  5/2019  Askar .................. H04L 5/1461
11,163,050 B2 * 11/2021  Bharadia ................ G01S 13/42
(Continued)

*Primary Examiner* — Junpeng Chen
(74) *Attorney, Agent, or Firm* — Run8 Patent Group, LLC; Peter Miller; Brian T. Chew (57) ABSTRACT

A system for generating a self-receive signal includes: a signal generator; a first signal processor; a second signal processor; and an antenna. The system also includes a first passive coupling device: defining a first input port electromagnetically coupled to the signal generator; defining a first transmitted port; defining a first coupled port electromagnetically coupled to the first signal processor; and characterized by a first phase balance between the first transmitted port and the first coupled port. The system further includes a second passive coupling device: defining a second input port electromagnetically coupled to the antenna; defining a second transmitted port electromagnetically coupled to the first transmitted port; defining a second coupled port electromagnetically coupled to the second signal processor; and characterized by a second phase balance between the second transmitted port and the second coupled port substantially similar to the first phase balance.

20 Claims, 4 Drawing Sheets

Related U.S. Application Data continuation of application No. 16/719,532, filed on Dec. 18, 2019, now Pat. No. 10,903,866.

(60) Provisional application No. 62/781,484, filed on Dec. 18, 2018.

(51) Int. Cl.
| | | |
|---|---|---|
| *C07G 1/00* | (2011.01) | |
| *C08B 37/00* | (2006.01) | |
| *C08H 7/00* | (2011.01) | |
| *D21C 11/00* | (2006.01) | |
| *H04B 1/16* | (2006.01) | |
| *H04B 1/40* | (2015.01) | |
| *H04B 17/14* | (2015.01) | |
| *H04L 5/00* | (2006.01) | |
| *H04L 7/00* | (2006.01) | |

(52) U.S. Cl.
CPC ............ *C08H 6/00* (2013.01); *D21C 11/0007* (2013.01); *H04B 1/16* (2013.01); *H04B 1/40* (2013.01); *H04B 17/14* (2015.01); *H04L 5/0048* (2013.01); *H04L 7/0079* (2013.01)

(56) References Cited

U.S. PATENT DOCUMENTS

| | | | | |
|---|---|---|---|---|
| 2007/0243838 | A1* | 10/2007 | Lang | H03F 3/189 |
| | | | | 455/114.2 |
| 2008/0274709 | A1* | 11/2008 | Goto | H04B 5/0062 |
| | | | | 455/272 |
| 2010/0159851 | A1* | 6/2010 | Endo | H04B 17/318 |
| | | | | 455/78 |
| 2011/0190028 | A1* | 8/2011 | Hahn | H03F 1/345 |
| | | | | 330/106 |
| 2012/0281772 | A1* | 11/2012 | Bailey | H04B 17/13 |
| | | | | 375/259 |
| 2015/0146765 | A1* | 5/2015 | Moffatt | H04B 1/40 |
| | | | | 375/219 |

* cited by examiner

SYSTEM FOR GENERATING ACCURATE REFERENCE SIGNALS FOR TIME-OF-ARRIVAL BASED TIME SYNCHRONIZATION

CROSS-REFERENCE TO RELATED APPLICATIONS

This application is a continuation application of U.S. patent application Ser. No. 17/129,682, filed on 21 Dec. 2020, which is a continuation application of U.S. patent application Ser. No. 16/719,532, filed on 18 Dec. 2019, which claims priority to U.S. Provisional Application No. 62/781,484, filed on 18 Dec. 2018, which is incorporated in its entirety by this reference.

This application is related to U.S. patent application Ser. No. 14/405,922, filed on 7 May 2019, which is incorporated in its entirety by this reference.

TECHNICAL FIELD

This invention relates generally to the field of transceiver design and more specifically to a new and useful system for generating self-receive synchronization signals in the field of transceiver design.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. First System

Figure 1:
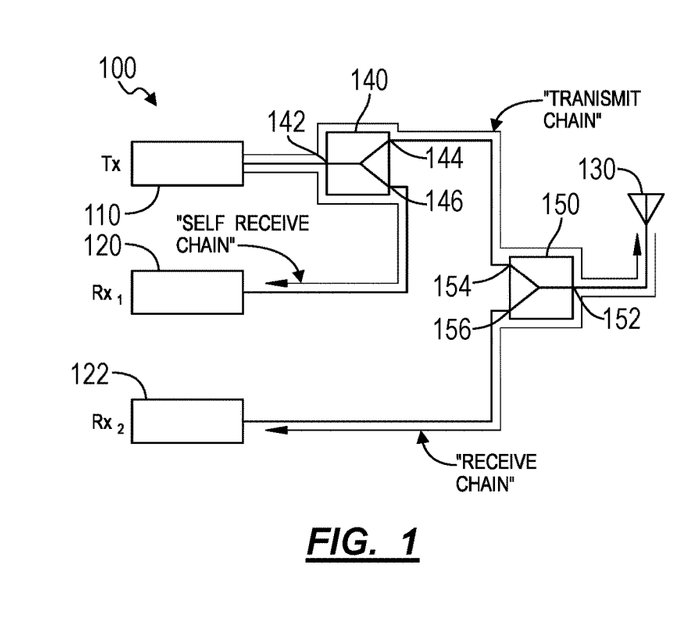
FIG. 1 is a schematic representation of a first system.

As shown in FIG. 1, a first system 100 (hereinafter "the system 100") for generating a self-receive signal includes: a signal generator 110; a first signal processor 120; a second signal processor 122; and an antenna 130. The system 100 also includes a first passive coupling device 140: comprising a first input port 142 electromagnetically coupled to the signal generator 110; comprising a first transmitted port 144; comprising a first coupled port 146 electromagnetically coupled to the first signal processor 120; and characterized by a first phase balance between the first transmitted port 144 and the first coupled port 146. The system 100 further includes a second passive coupling device 150: comprising a second input port 152 electromagnetically coupled to the antenna 130; comprising a second transmitted port 154 electromagnetically coupled to the first transmitted port 144; comprising a second coupled port 154 electromagnetically coupled to the second signal processor 122; and characterized by a second phase balance between the second transmitted port 154 and the second coupled port 156 substantially similar to the first phase balance.

Figure 2A:
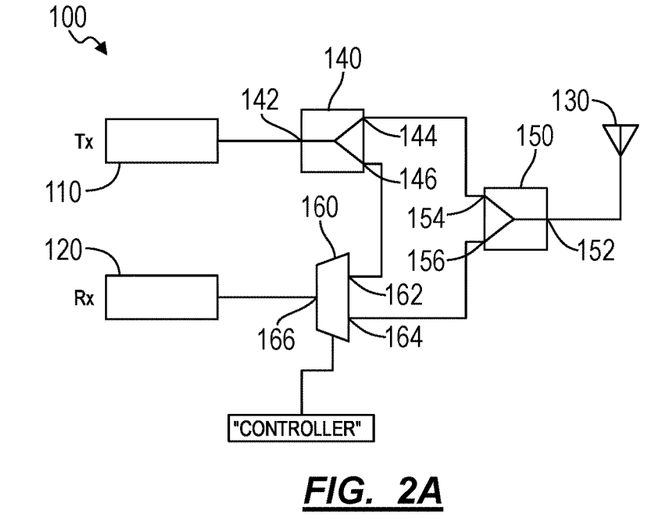
FIGS. 2A and 2B are schematic representations of the first system.

As shown in FIG. 2A, one variation of the system 100 includes: a signal generator 110; a signal processor 120; and an antenna 130. This variation of the system 100 also includes a multiplexer 160 comprising: a self-receive signal port 162; a receive signal port 164; and an output port 166 electromagnetically coupled to the signal processor 120. This variation of the system further includes a first passive coupling device 140: comprising a first input port 142 electromagnetically coupled to the signal generator 110; comprising a first transmitted port 144; comprising a first coupled port 146 electromagnetically coupled to the self-receive signal port 162; and characterized by a first phase balance between the first transmitted port 144 and the first coupled port 146. This variation of the system 100 also includes a second passive coupling device 150: comprising a second input port 152 electromagnetically coupled to the antenna 130; comprising a second transmitted port 154 electromagnetically coupled to the first transmitted port 144; comprising a second coupled port 156 electromagnetically coupled to the receive signal port 164; and characterized by a second phase balance between the second transmitted port 154 and the second coupled port 156 substantially similar to the first phase balance.

Figure 3A:
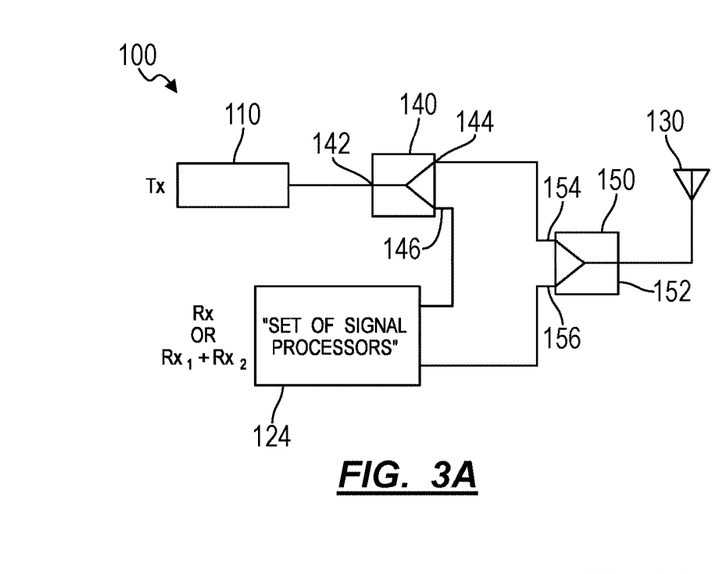
FIGS. 3A, 3B, and 3C are schematic representations of the first system.

As shown in FIG. 3A, one variation of the system 100 includes: a first signal generator 110; a first antenna 130; and a first set of signal processors 124. This variation of the system 100 also includes a first passive coupling device 140: comprising a first input port 142 electromagnetically coupled to the first signal generator 110; comprising a first transmitted port 144; comprising a first coupled port 146 electromagnetically coupled to the first set of signal processors 124; and characterized by a first phase balance between the first transmitted port 144 and the first coupled port 146. This variation of the system 100 further includes a second passive coupling device 150: comprising a second input port 152 electromagnetically coupled to the first antenna 130; comprising a second transmitted port 154 electromagnetically coupled to the first transmitted port 144; comprising a second coupled port 156 electromagnetically coupled to the first set of signal processors 124; and characterized by a second phase balance between the second transmitted port 154 and the second coupled port 156 substantially similar to the first phase balance.

1.1 Applications

Generally, the system 100 includes a single-antenna transceiver architecture that generates and receives reference signals (hereinafter "self-receive signals"), which are copies or reproductions of outgoing signals transmitted by the system 100. The system 100 generates and receives these self-receive signals without introducing significant group delay in the self-receive signal (when compared to the transmitted signal). Thus, the system 100 enables precise timestamping and phase comparison of self-receive signals with signals received via the antenna 130 of the system 100 (hereinafter "receive signals") in order to execute pairwise ranging and time synchronization protocols in cooperation with other instances of the system 100, which may be capable of estimating the time bias and the propagation delay between these instances of the system 100 to within one nanosecond.

More specifically, the system 100 includes a first passive coupling device 140 (e.g., directional coupler, power divider, circulator, etc.) electromagnetically coupled to the immediate output of the signal generator 110, which back-couples a reproduction of a signal output by the signal generator 110 to a signal processor of the system 100; and a second passive coupling device 150 coupling a transmit chain (including the signal generator no) and a receive chain (including a signal processor) to the antenna 130 of the system 100 to enable duplex communication of the system 100 via the single antenna 130. The system 100 includes a first passive coupling device 140 and a second passive coupling device 150 characterized by similar phase balance and group delay (specifically with respect to the frequency of an input signal) to ensure that any self-receive signal passing through the first passive coupling device 140 undergoes a similar phase shift, over the course of its internal transmission through the system 100, as a receive signal from the antenna 130 passing through the second passive coupling device 150. Thus, the system 100 can calculate a phase offset between a receive signal from its antenna 130 and a self-receive signal that is independent of the means by which the system 100 received these signals.

In a double receiver variation of the system 100, shown in FIG. 1, the system 100 includes: a first signal processor 120 (and an associated first receive chain) dedicated to receiving the back-coupled self-receive signal from the signal generator no via the first passive coupling device 140; and a second signal processor 122 (and an associated second receive chain) dedicated to receiving receive signals from the antenna 130 of the system 100. By including a dedicated signal-processor for each type of signal received, the system 100 minimizes the need to coordinate signals or perform switching operations, such as in a time-division multiple-access protocol (hereinafter "TDMA protocol"), thereby reducing the complexity of the system 100 at the expense of the inclusion of an additional set of receiver hardware.

In a single receiver variation of the system 100, shown in FIG. 2A, the system 100 includes a multiplexer 160 or power combiner 168, electromagnetically coupled to the input of the signal processor 120, which includes a self-receive port 162 (for self-receive signals) and a receive port 164 (for receive signals from the antenna 130). The system 100 can then include a controller (e.g., an FPGA or digital signal processor) configured to switch between these inputs according to a TDMA protocol, thereby providing the full functionality of the system 100 while utilizing only one signal processor, at the expense of greater protocol complexity.

In other implementations of the system 100, the system 100 can include additional components, such as attenuators 180 and low-noise amplifiers 190 along the self-receive chain (i.e. the propagation path of self-receive signals within the system 100) and the receive chain (i.e. the propagation path of receive signals within the system 100), which can be matched with regard to the group delays of these components. Additionally, the system 100 can include equal path lengths for the self-receive chain and the receive chain within the system 100.

1.2 Synchronization Example

One application of the system 100 includes a two-way synchronization protocol executed by a pair of nodes in a network, further described in U.S. patent application Ser. No. 16/405,922, where each node is an instance of the system 100. This synchronization protocol, when executed by instances of the system 100, can achieve sub-nanosecond time bias and propagation delay characterization, which, when implemented across a mesh network including many nodes, can enable precise localization of third-party devices and improved TDMA communication protocols between the nodes in the mesh network.

This synchronization protocol utilizes the time-of-arrival (hereinafter "TOA") of synchronization signals transmitted between the pair of nodes as well as the carrier phase of these synchronization signals. However, in measuring the TOA of any signal incident to a node, the node can only calculate a TOA for the signal after the signal propagates from the antenna 130, through the receive chain of the node, and to the signal processor of the node. Therefore, any TOA measured by a node is offset by the receive chain delay caused by the propagation of the signal through the receive chain of the node. Likewise, in measuring the carrier phase of any signal incident to a node, the node can only calculate a carrier phase of the signal after it has incurred a phase delay due to RF components in the receive chain of the node. Therefore, any calculations involving these TOAs or carrier phases must account for the values of these receive chain delays (in time and phase) of each node in the pair of nodes, either by precisely characterizing these delays or by including these delays on both sides of an equation and allowing these delays to cancel out during calculation of the time bias and propagation delay between the pair of nodes. While precise characterization of these delays to the sub-nanosecond level is technically difficult and may require specialized and/or expensive hardware, the system 100 can generate a reference signal that includes these receive chain delays with fairly inexpensive components, as further described below.

In this synchronization protocol, the nodes in the network are mutually connected to the internet or to a local area network such that the initial time bias between any pair of nodes in the mesh network is initially limited by the network time protocol (hereinafter "NTP"), or any other network time synchronization protocol. This time bias can range from tens of milliseconds to microseconds in many state-of-the-art networks.

Assuming an initial coarse clock synchronization between a pair of nodes (e.g. one to ten milliseconds), each node in the pair of nodes transmits a synchronization signal to the other node at a predetermined time according to each node's clock. However, due to the relative time bias between each of the nodes, these synchronization signals are sent at times offset by the time bias between the two nodes. Once the synchronization signal arrives at the antenna 130 of the opposite node in the pair of nodes, the synchronization signal propagates along the receive chain of the system 100, incurring a receive chain delay, which also results in a corresponding phase shift of this synchronization signal. Thus, when each node in the pair of nodes calculates a TOA of the synchronization signal, this TOA is offset by the time delay of the receive chain. Likewise, when each node calculates a carrier phase for the synchronization signal, this carrier phase is shifted based on the phase shift of the receive chain.

Upon sending the synchronization signal, each node in the pair of nodes also generates a self-receive signal, which is an attenuated repetition of the outgoing synchronization signal. The system 100 generates this self-receive signal by back-coupling the synchronization signal, via a first passive coupling device 140, along a self-receive chain of the system 100 to a signal processor of the system 100. Because the system 100 includes a self-receive chain that is characterized by a similar time delay (e.g., within than one nanosecond) relative to the time delay of the receive chain and a similar phase shift (e.g., a few degrees) relative to the phase shift of the receive chain, the TOA of the self-receive signal and the carrier phase of the self-receive signal are offset by a substantially similar time delay and a substantially similar phase shift to those incurred by the synchronization signal upon reception by the system 100.

Thus, the TOA of the self-receive signal acts as a time-of-departure of the synchronization signal approximately offset by the time delay of the receive chain of the transmitting node, while the carrier phase of the self-receive signal acts as a "carrier-phase-of-departure" for the synchronization signal approximately offset by the phase shift of the receive chain of the transmitting node.

Therefore, while executing this synchronization protocol, each node in the pair of nodes has recorded a TOA and a carrier phase for one self-receive signal and for one synchronization signal received from the opposite node resulting in four TOA values and four carrier phase values. A system executing this time synchronization protocol can then solve a system of equations based on the four TOA values, algebraically canceling out the time delays of the receive chains of each node, in order to calculate the time bias and propagation time between the pair of nodes.

More specifically, a first node and a second node in the pair of nodes and/or a remote system communicating with these nodes can be configured to execute a two-way time synchronization protocol by, at the first node: transmitting a first synchronization signal; and generating a first self-receive signal based on the first synchronization signal. Then the second node can: transmit a second synchronization signal; and generate a second self-receive signal based on the second synchronization signal. Once the first node and the second node have each transmitted a synchronization signal and generated a self-receive signal, the first node can: calculate a first time-of-arrival of the first self-receive signal; and calculate a second time-of-arrival of the second synchronization signal. The second node can then: calculate a third time-of-arrival of the second self-receive signal; and calculate a fourth time-of-arrival of the first synchronization signal. Then a system in communication with the first node and the second node or one of the nodes themselves can calculate a time bias and a propagation delay between the first node and the second node based on the first time-of-arrival, the second time-of-arrival, the third time-of-arrival, and the fourth time-of-arrival.

A system executing this time synchronization protocol can then further refine this time bias and propagation time calculation utilizing the four carrier phase values generated by the pair of nodes. Therefore, the system 100 can enable characterization of the time bias between a pair of nodes and the propagation time between the pair of nodes.

For a double signal processor variation of the system 100, the system 100 can include: a self-receive chain that electromagnetically couples the signal generator 110 to the first signal processor 120 via the first passive coupling device 140 and is configured to back-couple a transmitted signal from the signal generator 110 for reception at the first signal processor 120 as a self-receive signal; and a receive chain that electromagnetically couples the antenna 130 to the second signal processor 122 via the second passive coupling device 150 and is configured to couple a signal received at the antenna 130 for reception at the second signal processor 122. Additionally, the system 100 can include a first signal processor configured to, subsequent to reception of the self-receive signal, calculate a time-of-arrival of the self-receive signal based on the clock of the system 100, the time-of-arrival approximating a time-of-departure for the transmitted signal according to the clock of the system 100.

For a single signal processor variation of the system 100, the system 100 can include: a self-receive chain that electromagnetically couples the signal generator 110 to the signal processor 120 via the first passive coupling device 140 and the multiplexer 160 and is configured to back-couple a transmitted signal from the signal generator 110 for reception at the signal processor 120 as a self-receive signal; and a receive chain that electromagnetically couples the antenna 130 to the signal processor 120 via the second passive coupling device 150 and the multiplexer 160 and is configured to couple a signal received at the antenna 130 for reception at the signal processor 120. Additionally, the system 100 can include a first signal processor configured to, subsequent to reception of the self-receive signal, calculate a time-of-arrival of the self-receive signal based on the clock of the system 100, the time-of-arrival approximating a time-of-departure for the transmitted signal according to the clock of the system 100.

1.3 Hardware

Generally, the system 100 is included in or is an instance of an RF transceiver and includes RF hardware such as a superheterodyne radio architecture, or other RF front-end architecture such as direct conversion, direct-IF conversion, or zero-IF conversion, and a transmit-receive antenna 130. The system 100 includes a transmit chain, a receive chain, and a self-receive chain. The transmit chain includes a series of hardware components that process transmitted signals generated by a signal generator 110 (e.g., an FPGA or DSP) and feed them toward an antenna 130. The receive chain is characterized by a receive signal path includes a series of hardware components that process signals received at the antenna 130 and directs receive signals from the antenna 130 to a signal processor of the system 100. The self-receive chain is characterized by a self-receive signal path and includes a series of hardware that generate, back-couple (e.g., within the system 100), and process self-receive signals. The components included within the transmit chain, the receive chain, and the self-receive chain can overlap (e.g., via passive or active coupling devices).

In one implementation, the signal generator 110 of the system 100 is configured to generate complex digital signals and output the generated signals to a DAC along the transmit chain and the self-receive chain. The complex components of the digital signals represent the in-phase and quadrature portions (i.e. I/Q) of the analog signal to be generated by the DAC. Additionally, the signal processor of the node receives digital signals from the antenna 130 of the system 100 via an ADC. The system 100 can also include a software-defined radio architecture performing the function of any of the hardware elements described above.

In an alternate implementation, the system 100 can integrate with a wired communication system 100. In this implementation, the system 100 can include an I/O port and/or appropriate interface converters for communicating over any wired medium (e.g. ethernet, fiber optic, etc.) instead of an antenna 130.

The system 100 can also include a clock, such as a crystal oscillator clock or an atomic clock, which can be responsible for time-keeping functions at the system 100. In one example, the clock is a quartz crystal oscillator with an AT cut and a clock frequency of ten megahertz. However, the system 100 can include a crystal oscillator of any frequency or cut. Additionally, the system 100 can include oven-controlled crystal oscillators. The clock of the system 100 can generate a timestamp counter (e.g., a sampling clock signal) for one or more ADCs of the system 100. Furthermore, the clock can also generate a timestamp counter for the digital-to-analog converter (hereinafter "DAC") of the system 100, thereby synchronizing, in the frequency and phase domain, the timestamps calculated by the system 100.

Although the system 100 is described with reference to RF transceiver hardware and with respect to RF signals, the system 100 can be configured to transmit and receive signals in other media. For example, the system 100 can be integrated into an optical transceiver or a sonic transceiver (e.g., sonar).

In one variation, the system 100 can include a set of two signal processors. In this variation, a first signal processor 120 in the set of signal processors 124 is electromagnetically coupled to the termination of the self-receive chain and is thus configured to receive and process self-receive signals from the signal generator 110 of the system 100. The second signal processor 122 is electromagnetically coupled at the termination of the receive chain and is thus configured to receive and process receive signals from the antenna 130 of the system 100. This variation is described in further detail below.

In another variation, the system 100 can include a single signal processor that is electromagnetically coupled to an output of a multiplexer 160 or a power combiner 168 and is thus configured to receive and process signals from both the receive chain and the self-receive chain of the system 100. This variation is described in further detail below.

1.3.1 First Passive Coupling Device

Generally, the system 100 can include a first passive coupling device 140—such as a directional coupler or a power divider—that is interposed along the transmit chain and self-receive chain of the system 100 and electromagnetically coupled to the output of the signal generator 110 and any associated RF components described above, thereby bifurcating a signal generated by the signal generator 110 along the transmit chain and the self-receive chain simultaneously. More specifically, the system 100 can include: a first passive coupling device 140: defining an input port 142 electromagnetically coupled to the signal generator 110; defining a transmitted port 144 electromagnetically coupled to the second passive coupling device 150; defining a first coupled port 146 electromagnetically coupled to a signal processor 120 (via the self-receive chain); and characterized by a first phase balance between the first transmitted port 144 and the first coupled port 146 and a first group delay. Thus, the first passive coupling device 140 functions to redirect a portion of a transmitted signal toward a signal processor 120 of the system 100 in order to generate a self-receive signal based on the transmitted signal. The first passive coupling device 140 is also characterized by a group delay and phase balance that can be closely matched to the second passive coupling device 150, which functions to couple the antenna 130 to the receive chain. Therefore, self-receive signals propagating through the first passive coupling device 140 may be imparted with a substantially similar group delay to receive signals propagating through the second passive coupling device 150.

In one implementation, the system 100 includes a 50/50 power divider or hybrid coupler as the first passive coupling device 140. Thus, signals incident upon this power divider are evenly split between the transmit chain and the self-receive chain. In this implementation, in order to prevent saturation of the ADC of a signal processor along the self-receive chain, the system 100 can also include an attenuator 180 along the self-receive chain. Additionally or alternatively, the system 100 can include a power amplifier 170 electromagnetically interposed between the first passive coupling device 140 and the second passive coupling device 150 in order to increase the power of the signal before transmission via the antenna 130.

In another implementation, the system 100 can include a directional coupler as the first passive coupling device 140, which can further include an input port 142, a transmitted port 144 (i.e. a through port) and a coupled port 146. In this implementation, the input port 146 is electromagnetically coupled to the output of the signal generator 110, the transmitted port 144 is electromagnetically coupled to the second passive coupling device 150 and then to the antenna 130, and the coupled port 146 is electromagnetically coupled to a signal processor 120 of the system 100 via the self-receive chain. The system 100 can include a directional coupler characterized by a coupling factor such that a signal back-coupled by the directional coupler along the self-receive chain does not saturate the ADC of the signal processor 120.

1.3.2 First Signal Processor

Generally, in the variation of the system 100 including a set of two signal processors (shown in FIG. 1), the system 100 can include a first signal processor 120 in the set of signal processors 124 electromagnetically coupled to a coupled port 146 of the first passive coupling device 140. More specifically, the first signal processor 120 can receive and process self-receive signals back-coupled by the first passive coupling device 140. Thus, first signal processor 120 can function to receive self-receive signals at the termination of the self-receive chain of the system 100.

In one implementation, the first signal processor 120 can include an ADC characterized by a narrow range and high-resolution in comparison to a second signal processor 122 in the set of signal processors 124 because the system 100 can tightly control the signal strength of the self-receive signal at the signal generator 110 or at a variable attenuator 180 interposed between the first passive coupling device 140 and the first signal processor 120.

1.3.3 Second Passive Coupling Device

Generally, the system 100 includes a second passive coupling device 150—such as a directional coupler or power divider—electromagnetically connecting the transmit chain to the antenna 130 and the antenna 130 to the receive chain. More specifically, the system 100 includes a second passive coupling device 150: defining an input port 152 electromagnetically coupled to the antenna 130; defining a transmitted port 154 electromagnetically coupled to the transmitted port 144 of the first passive coupling device 140; defining a second coupled port 156 electromagnetically coupled to the second signal processor 122; and characterized by a second phase balance between the transmitted port 154 and the coupled port 156 substantially similar to the first phase balance and a second group delay substantially similar to the group delay of the first passive coupling device 140. Thus, the second passive coupling device 150 enables the system 100 to use one antenna 130 (or I/O port) for both transmitting and receiving functions. Therefore, the passive coupling device also functions to transmit signals from the signal generator 110 to the antenna 130 and from the antenna 130 to a signal processor. Thus, the system 100 can include any device that may satisfy the above constraints, such as a directional coupler, a power divider, a circulator, or any other transmission line coupling device. However, in order to maintain similarities in phase balance and group delay to the first passive coupling device 140, the system 100 can include a second passive coupling device 150 that is the same type of coupling device (or the exact same component) as the first coupling device. By including a first passive coupling device 140 and a second passive coupling device 150 with similar characteristics, the system 100 can ensure that the self-receive chain and the receive chain impart a similar time delay and phase shift to signals propagating through these chains.

In one example, where the system 100 includes a first power divider as the first passive coupling device 140, the system 100 can also include a second power divider as the second passive coupling device 150. In another example, where the system 100 includes a first directional coupler as the first passive coupling device 140, the system 100 also includes a second directional coupler as the second passive coupling device 150.

In one implementation, the system 100 includes a second passive coupling device 150 that electromagnetically couples the antenna 130 to a signal processor of the system 100 via the same port configuration of the first passive coupling device 140 that electromagnetically couples the signal generator no to the signal processor. For example, the system 100 can include the first passive coupling device 140 defining an input port 142 electromagnetically coupled to the signal generator no and a coupled port 144 electromagnetically coupled to the signal processor 120 for the self-receive chain. Therefore, in this example, the system 100 also includes the second passive coupling device 150, which includes an input port 152 electromagnetically coupled to the antenna 130 and a coupled port 156 electromagnetically coupled to the signal processor for the receive chain.

1.3.4 Antenna

Generally, the system 100 includes an antenna 130 electromagnetically coupled to the second passive coupling device 150, to enable the system 100 to transmit and receive signals via the antenna 130. More specifically, the system 100 includes an antenna 130 electromagnetically coupled to an input port 152 of the second passive coupling device 150, thereby enabling full-duplex transmission and reception between the system 100 and another transceiver. The system 100 can include an antenna 130 type appropriate for an RF spectrum of the system 100 (e.g., the magnitude and bandwidth of signals transmitted by the system 100), a desired range of the system 100, and the RF environment of the system 100. Additionally, the system 100 can include antenna 130 designs such as a bowtie antenna or other self-complementary antennas in order to impart a flat group delay to signals received and/or transmitted by the system 100. Additionally, the system 100 can include an impedance matching network between the second passive coupling device 150 and the antenna 130 in order to improve power efficiency and reduce reflections at the antenna interface.

1.3.5 Second Signal Processor

Generally, as shown in FIG. 1, the system 100 includes a second signal processor 122 configured to process signals received at the antenna 130 of the system 100. More specifically, the system 100 includes: the antenna 130 electromagnetically coupled to an input port 152 of the second passive coupling device 150, the second passive coupling device 150 defining a coupled port 156 that is electromagnetically coupled to a second signal processor 122 in the set of signal processors 124. Thus, when the system 100 receives signals at the antenna 130, they are propagated through the second passive coupling device 150 to a second signal processor 122. The system 100 can also include a set of filters, low-noise amplifiers 190, or other components to condition the signal received from the antenna 130 for improved signal processing.

In one implementation, the system 100 can include a second signal processor 122 that further includes an ADC with a wider range and lower resolution when compared to the first signal processor 120, such that the system 100 can receive signals from other transceivers with a larger variation in SNR when compared to the self-receive signal generated by the system 100.

1.3.6 Single Signal Processor Variation

Figure 2B:
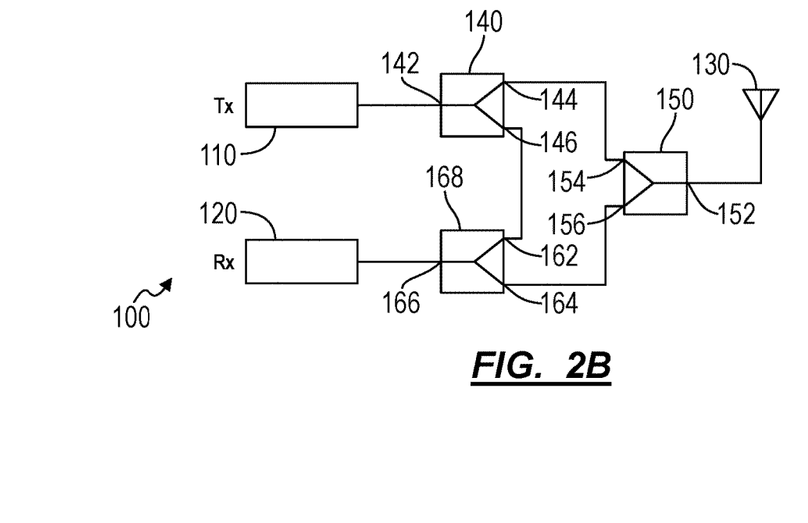

Generally, in the variation shown in FIGS. 2A and 2B, the system 100 includes one signal processor for both the self-receive chain and the receive chain. More specifically, the system 100 can include: an antenna 130 electromagnetically coupled to the second passive coupling device 150, the second passive coupling device 150 defining a coupled port 156 that is electromagnetically coupled to the first signal processor 120. In particular, the system 100 can include a multiplexer 160 or power combiner 168 that couples both the self-receive chain (via the first passive coupling device 140) and the receive chain (via the second passive coupling device 150) to the single signal processor of the system 100. This variation of the system 100 reduces unit costs by including only a single signal processor at the expense of protocol complexity (e.g., to prevent interference of between a simultaneously received self-receive signal and a signal received from the antenna 130).

1.3.6.1 Multiplexer and Digital Controller

Generally, in the single signal processor variation shown in FIG. 2A, the system 100 can include a multiplexer 160 coupled to a digital controller—such as an FPGA or digital signal processor—to actively switch between the self-receive chain and the receive chain of the system 100 and receive both self-receive signals and receive signals respectively. More specifically, the system 100 can include: a multiplexer 160; and a digital controller electromagnetically coupled to the multiplexer 160 and configured to: select the self-receive signal port 162 during a transmit slot in a TDMA frame; and select the receive signal port 164 during a receive slot in the TDMA frame. Thus, in this implementation, the system 100 is configured to transmit signals and concurrently generate self-receive signals during a first slot of a TDMA frame and receive signals from other transceivers during subsequent slots of a TDMA frame.

Furthermore, the system 100 can include further comprising a self-receive chain: electromagnetically coupling the signal generator no to the signal processor 120 via the first passive coupling device 140 and the multiplexer 160 and configured to back-couple a transmitted signal from the signal generator 110 for reception at the signal processor 120 as a self-receive signal during the transmit slot in the time-division multiple access frame; and a receive chain: electromagnetically coupling the antenna 130 to the signal processor 120 via the second passive coupling device 150 and the multiplexer 160 and configured to couple a signal received at the antenna 130 for reception at the signal processor 120 during the receive slot in the time-division multiple access frame.

1.3.6.2 Power Combiner

Generally, in the single signal processor variation shown in FIG. 2B, the system 100 can include a power combiner 168 such that the system 100 can concurrently receive a self-receive signal and a receive signal (e.g., via a frequency division multiple access protocol). More specifically, the system 100 can include a power combiner 168: defining a self-receive signal port 162 electromagnetically coupled to the coupled port 146 of the first passive coupling device 140; defining a receive signal port 164 electromagnetically coupled to the coupled port 156 of the second passive coupling device 150; and defining a combined port 166 electromagnetically coupled to the signal processor 120. Thus, the power combiner 168 can merge the self-receive chain and the receive chain into the signal processor enable the system 100 to generate self-receive signals and perform transceiving functions with a single signal processor 120.

1.3.7 Power Amplifier

Figure 3B:
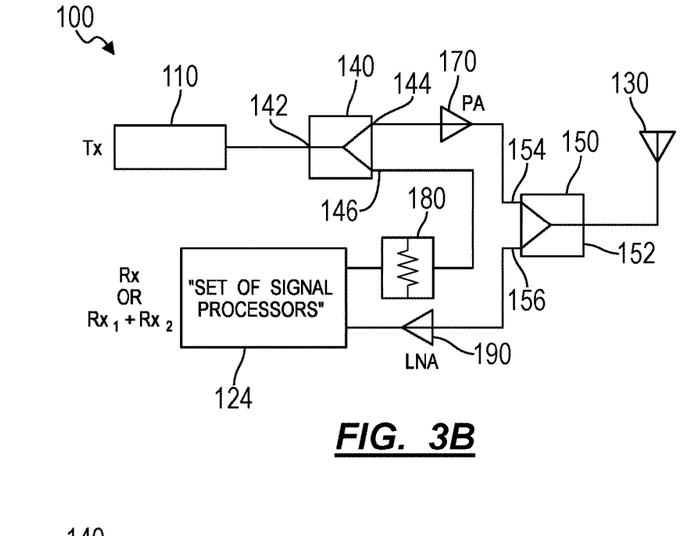
Figure 3C:
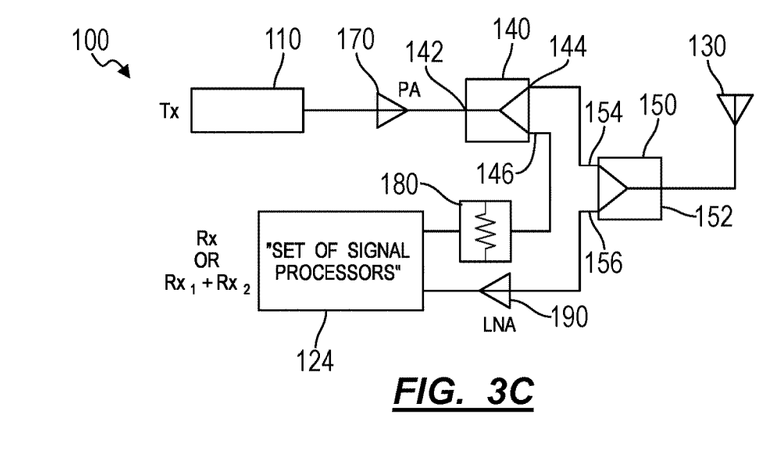

In one implementation, shown in FIGS. 3B and 3C, the system 100 can include a power amplifier 170 along the transmit chain in order to boost the power of a signal generated by the signal processor prior to transmission via the antenna 130. More specifically, the system 100 can include a power amplifier 170 electromagnetically interposed between the first transmitted port 144 and the second transmitted port 154. In this implementation, the system 100 can amplify a transmitted signal after the signal has propagated through the first passive coupling device 140 (as shown in FIG. 3B), thereby generating the self-receive signal. Thus, the system 100 ensures that the self-receive signal is back-coupled toward the signal processor at a lower power, thereby preventing saturation of the ADC of the signal processor. The placement of the power amplifier 170 subsequent to the first passive coupling device 140 along the transmit chain can enable the user of a lower range ADC of the signal processor for implementations of the system 100 including a single signal processor. In this implementation, because the self-receive signal is not amplified, while the transmitted signal is amplified, the system 100 can include a power amplifier 170 that imparts a small (e.g., less than five degree) phase shift or a well characterized phase shift to the transmitted signal to minimize differences in phase between the self-receive signal and the transmitted signal, while propagating through the transmit chain and the self-receive chain respectively.

In an alternative implementation, shown in FIG. 3C, the system 100 can include a power amplifier 170 electromagnetically interposed between the signal generator 110 and the first input port 142. Thus, in this implementation, a transmitted signal is amplified by the power amplifier 170 prior to being back-coupled by the first passive coupling device 140, thereby improving parity between the transmit chain and the self-receive chain (e.g., in terms of the phase shift and time delay). More specifically, the system 100 includes a self-receive chain: electromagnetically coupling the signal generator 110 to the first signal processor 120 via the power amplifier 170 and the first passive coupling device 140 and configured to back-couple a transmitted signal from the signal generator no for reception at the first signal processor 120 effected by the first group delay; and a transmit chain: electromagnetically coupling the signal generator no to the antenna 130 via the first passive coupling device 140 and the second passive coupling device 150 and configured to couple the transmitted signal generated at the signal generator 110 for transmission at the antenna 130 effected by the first group delay.

However, in this implementation, the self-receive signal is also amplified prior to being back-coupled to the transceiver the system 100 can also include an attenuator 180 interposed between the coupled port 146 of the first passive coupling device 140 and the signal processor 120 configured to reduce the signal power of the self-receive signal in order to prevent saturation of the ADC of the signal processor 120.

1.3.8 Low-Noise Amplifier and Attenuator

In one implementation, shown in FIGS. 3B and 3C, the system 100 includes an attenuator 180 in order to reduce the power of the self-receive signal thereby preventing saturation of the ADC of a signal processor on the self-receive chain. Additionally, the system 100 can also include a low-noise amplifier 190 to boost the SNR of signals received from the antenna 130. Furthermore, the system 100 can substantially match the phase shift and/or time delay (i.e., group delay) imparted by these components to ensure parity in phase shift and time delay between the self-receive chain and the receive-chain. More specifically, in the double signal processor variation the system 100 can include: an attenuator 180 electromagnetically interposed between the first coupled port 146 and the first signal processor 120 and defining a first group delay; and a low-noise amplifier 190 electromagnetically interposed between the second coupled port 156 and the second signal processor 122 and defining a second group delay substantially similar to the first group delay. In the single signal processor variation, the system 100 can include: an attenuator 180 electromagnetically interposed between the first coupled port 146 and the self-receive signal port 162 and defining a first group delay; and a low-noise amplifier 190 electromagnetically interposed between the second coupled port 156 and the receive signal port 164 and defining a second group delay substantially similar to the first group delay.

1.4 Signal Path Length and Group Delay Parity

In one implementation, the system 100 can define a self-receive chain that is characterized by a signal path length that is the substantially similar (e.g., within three millimeters) of a signal path length of the receive chain, thereby ensuring a self-receive chain propagation delay that is substantially the same as the receive chain propagation delay. Therefore, the system 100 can directly compare TOAs of self-receive signals and receive signals at the transceiver. More specifically, in the double signal processor variation, the system 100 can include a self-receive chain: electromagnetically coupling the signal generator 110 to the first signal processor 120 via the first passive coupling device 140 and defining a self-receive signal path length; and a receive chain electromagnetically coupling the antenna 130 to the second signal processor 122 via the second passive coupling device 150 and defining a receive signal path length substantially equal to the self-receive signal path length. Alternatively, in the single signal processor variation, the system 100 can include: a self-receive chain electromagnetically coupling the signal generator no to the signal processor via the first passive coupling device 140 and defining a self-receive signal path length; and a receive chain electromagnetically coupling the antenna 130 to the signal processor via the second passive coupling device 150 and defining a receive signal path length substantially equal to the self-receive signal path length.

In another implementation, the system 100 can also define a self-receive chain and a receive chain characterized by substantially equal group delay in order to ensure parity between self-receive signals received by the system 100 and receive signals received by the system 100. More specifically, the system can include: a self-receive chain configured to back-couple the transmitted signal from the signal generator for reception at the first signal processor with a first group delay; and a receive chain configured to couple the signal received at the antenna for reception at the second signal processor with a second group delay substantially similar to the first group delay.

2. Second System

Figure 4:
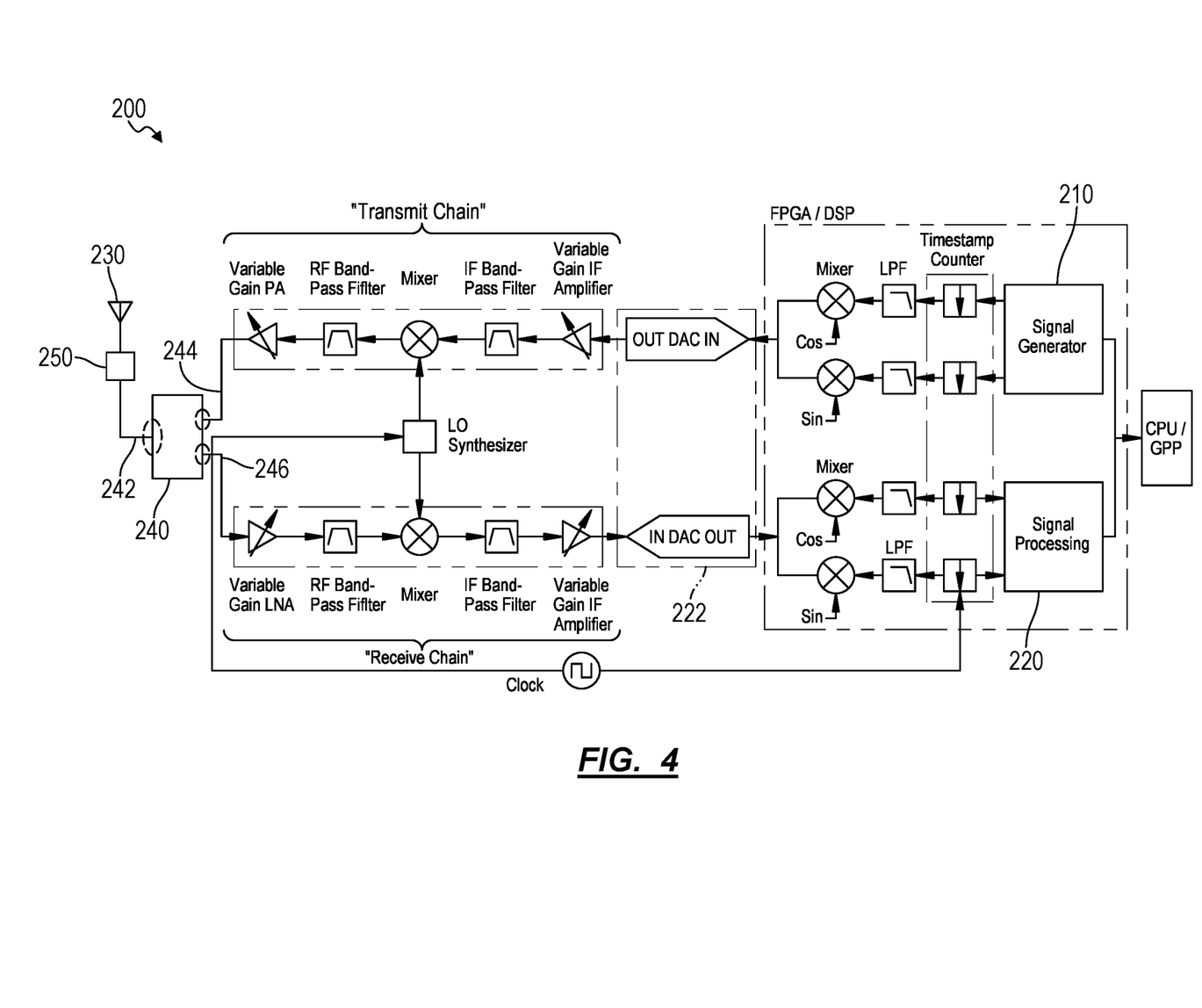
FIG. 4 is a schematic representation of a second system.

As shown in FIG. 4, a second system 200 (hereinafter "the system 200") for generating a self-receive signal includes: a signal generator 210 configured to generate a signal at a transmit voltage; a signal processor 220 comprising an analog-to-digital converter 222 (hereinafter "ADC 222") characterized by an input noise floor and an input saturation voltage; and an antenna 230 characterized by an antenna impedance. The system 200 also includes a passive coupling device 240: characterized by a characteristic impedance; comprising an antenna port 242 electromagnetically coupled to the antenna 230; comprising a transmit port 244 electromagnetically coupled to the signal generator 210; and comprising a receive port 246 electromagnetically coupled to the signal processor 220. The system 200 further includes an impedance matching network 250: electromagnetically interposed between the antenna port 242 and the antenna 230; and configured to shift the antenna impedance to a load impedance different from the characteristic impedance of the passive coupling device 240. Additionally, the antenna 230 and the passive coupling device 240 cooperate to reflect the signal, transmitted via the transmit port 244 and at the transmit voltage, toward the receive port 246 at a receive voltage between the input noise floor and the input saturation voltage according to a reflection coefficient effected by a difference between the load impedance and the characteristic impedance.

In one variation, the system 200 can include an impedance matching network 250: electromagnetically interposed between the antenna port 242 and an antenna 230; and configured to reflect the signal from the signal generator 210 at the transmit voltage toward the signal processor 220 at a receive voltage between the input noise floor and the input saturation voltage.

In another variation, the system 200 can include an impedance matching network 250: electromagnetically interposed between the antenna port 242 and an antenna 230; and configured to transform the antenna impedance of the antenna 230 to a load impedance, the load impedance configured to reflect signals transmitted from the transmit port 244 and at the transmit voltage toward the receive port 246 at a receive voltage between the input noise floor and the input saturation voltage.

2.1 Applications

Generally, the system 200: includes a passive coupling device 240 (e.g., directional coupler, power divider, circulator, etc.) coupled to an impedance matching network 250; and interfaces with or includes a transceiver (e.g., including an antenna 230 configured to transmit and receive RF signals) in order to enable calculation of a departure time for a transmitted signal that is offset by a receive chain delay in the transceiver, thereby enabling precise temporal calibration with another transceiver. The passive coupling device 240 can couple to a transmit chain and a receive chain (which can include amplifiers, filters, mixers, etc.) within the transceiver. The transmit chain and the receive chain can be further coupled to a signal generator 210 and a signal processor 220 respectively (e.g., a field-programmable gate array or digital signal processor 220).

In particular, the system 200 is configured to reflect a signal transmitted by the signal generator 210—via the transmit chain—such that the power of the reflection—propagated through the receive chain—falls within a detectable range of the signal processor 220 by controlling an impedance mismatch between the characteristic impedance of the passive coupling device 240 and the load impedance of the antenna 230. By reflecting a transmitted signal at the interface between the passive coupling device 240 and the antenna 230, the system 200 ensures that the reflected portion of the transmitted signal (hereinafter "the self-receive signal") propagates through the same receive chain as any signal received by the antenna 230 and therefore incurs the same receive chain delay as any received signal.

Therefore, when calculating a first propagation time for a first synchronization signal transmitted by a first transceiver to a second transceiver (wherein each transceiver includes an instance of the system 200), the first transceiver can calculate a departure time of the first synchronization signal offset by a receive chain delay of the first transceiver. Similarly, when calculating a second propagation time for a second synchronization signal transmitted by the second transceiver to the first transceiver, the second transceiver can calculate a departure time of the second synchronization signal offset by a receive chain delay of the second transceiver. The second transceiver can then calculate an arrival time of the first synchronization signal while the first transceiver can calculate an arrival time of the second synchronization signal offset by the receive chain delay of the second and first transceiver respectively. The transceivers can then transmit the departure times of the first and second synchronization signals and the arrival times of the first and second synchronization signals to a computational device. Because the departure times are offset by the same receive chain delays as the arrival times, the computational device can calculate propagation times of the synchronization signals without having to characterize the receive chain delay of either transceiver.

Additionally, by generating self-receive signals at the interface between the passive coupling device 240 and the antenna 230 of the transceiver, the system 200 circumvents the need to include a second antenna in the transceiver to enable timestamping the departure times of a transmitted signal offset by the receive chain delay The system 200 self-reflects signals at the interface between the passive coupling device 240 and the antenna 230 by including an impedance matching network 250 between the antenna 230 and the passive coupling device 240. The impedance matching network 250 transforms the impedance of the antenna 230 to an impedance that effects a precise reflection coefficient between the passive coupling device 240 and the antenna 230. The reflection coefficient is selected such that the reflected power of the self-receive signal is above the noise floor of the ADC 222 and below the saturation voltage of the ADC 222.

Furthermore, the impedance matching network 250 can maintain the reflection coefficient for a wide range of signal frequencies. For example, the system 200 can include a switchable wideband matching network to improve the consistency of the reflection coefficient across a wide range of transmit frequencies. In this example, the system 200 can actively switch between multiple impedance matching networks 250 depending on the frequency of the signal being transmitted by the system 200.

In another example, the system 200 can include a frequency multiplexer connected to multiple impedance matching networks 250 such that each distinct impedance matching network 250 encounters signals at a frequency that results in the precise reflection coefficient.

In yet another example, the system 200 can include an adaptive impedance matching network 250 that can adjust its impedance and therefore the reflection coefficient between the passive coupling device 240 and the antenna 230. The system 200 can then adjust the reflection coefficient to ensure that the self-receive signal is well received despite changes in the noise levels being received at the ADC 222 due to changing gains in RF transmit chain and/or receive chain amplifiers and/or interfering signals in the frequency band or bands of interest.

In addition to the impedance matching network 250 at the antenna port 242, the system 200 can also include impedance matching networks 250 at each of the transmit port 244 and the receive port 246 to improve signal power transfer between the transmit chain and the passive coupling device 240 and the passive coupling device 240 and the receive chain respectively.

In one implementation, the system 200 includes a directional coupler as the passive coupling device 240. The directional coupler includes four ports, two for each of the coupled transmission lines. In this implementation, the transmit port 244 and the antenna port 242 are located on the same transmission line in the directional coupler while the receive port 246 is located at the coupled port opposite the antenna 230, thereby receiving coupled power from the antenna 230 and reflected power from the interface between the directional coupler and the antenna 230. Alternatively, the system 200 can include a directional coupler wherein the receive port 246 and the antenna port 242 are located on the same transmission line. As a result, the receive port 246 receives direct power from the antenna port 242 and the reflected power from the antenna port 242. However, in this alternative implementation, the antenna port 242 receives signals from the transmit port 244 at a lower power due to coupling between the two transmission lines. Thus, a higher power at the transmit port 244 results in the same power at the antenna port 242. However, in an implementation of the receive port 246 and the antenna port 242 coupled to the same transmission line, the system 200 can improve the sensitivity of the transceiver to signals received at the antenna 230.

In an alternative implementation, the system 200 includes a power divider as the passive coupling device 240. The power divider divides power from an input port between two output ports. In this implementation, power input at the antenna port 242 is split between the transmit port 244 and the receive port 246, thus any power reflected at the interface between the antenna 230 and the power divider is also divided between the transmit port 244 and the receive port 246.

In yet another implementation, the system 200 includes a circulator as the passive coupling device 240. The circulator can couple the transmit port 244 directly to the antenna port 242 while the antenna port 242 is directly coupled to the receive port 246. Any reflections generated at the antenna port 242 interface are then coupled back to the receive port 246.

In addition to generating self-receive signals in a RF transceiver, the system 200 can also be applied to transceivers in other communication media. For example, the system 200 can also include optical signal generator 210s, optical signal processor 220s, and optical passive coupling device 240s, and can similarly produce an optical self-receive signal via precise control of the optical impedance match at an interface of an optical output port (corresponding to the antenna port 242 in a transceiver). In other examples, the system 200 can be integrated with an active sonar system to generate self-receive sound waves for similar time-synchronization or other purposes.

2.2 Synchronization Example

One application of the system 200 includes a two-way synchronization protocol executed by a pair of nodes in a network, further described in U.S. patent application Ser. No. 16/405,922, where each node is an instance of the system 200. This synchronization protocol, when executed by instances of the system 200, can achieve sub-nanosecond time bias and propagation delay characterization, which, when implemented across a mesh network including many nodes, can enable precise localization of third-party devices and improved TDMA communication protocols between the nodes in the mesh network.

This synchronization protocol utilizes the time-of-arrival (hereinafter "TOA") of synchronization signals transmitted between the pair of nodes as well as the carrier phase of these synchronization signals. However, in measuring the TOA of any signal incident to a node, the node can only calculate a TOA for the signal after the signal propagates from the antenna 230, through the receive chain of the node, and to the signal processor 220 of the node. Therefore, any TOA measured by a node is offset by the receive chain delay caused by the propagation of the signal through the receive chain of the node. Likewise, in measuring the carrier phase of any signal incident to a node, the node can only calculate a carrier phase of the signal after it has incurred a phase delay due to RF components in the receive chain of the node. Therefore, any calculations involving these TOAs or carrier phases must account for the values of these receive chain delays (in time and phase) of each node in the pair of nodes, either by precisely characterizing these delays or by including these delays on both sides of an equation and allowing these delays to cancel out during calculation of the time bias and propagation delay between the pair of nodes. While precise characterization of these delays to the sub-nanosecond level is technically difficult and may require specialized and/or expensive hardware, the system 200 can generate a reference signal that includes these receive chain delays with fairly inexpensive components, as further described below.

In this synchronization protocol, the nodes in the network are mutually connected to the internet or to a local area network such that the initial time bias between any pair of nodes in the mesh network is initially limited by the network time protocol (hereinafter "NTP"), or any other network time synchronization protocol. This time bias can range from tens of milliseconds to microseconds in many state-of-the-art networks.

Assuming an initial coarse clock synchronization between a pair of nodes (e.g. one to ten milliseconds), each of the pair of nodes transmits a synchronization signal to the other node at a predetermined time according to each node's clock. However, due to the relative time bias between each of the nodes, these synchronization signals are sent at times offset by the time bias between the two nodes. Once the synchronization signal arrives at the antenna 230 of the opposite node in the pair of nodes, the synchronization signal propagates along the receive chain of the system 200 incurring a receive chain delay, which also results in a corresponding phase shift of this synchronization signal. Thus, when each node in the pair of nodes calculates a TOA of the synchronization signal, this TOA is offset by the time delay of the receive chain. Likewise, when each node calculates a carrier phase for the synchronization signal, this carrier phase is shifted based on the phase shift of the receive chain.

Upon sending the synchronization signal, each node in the pair of nodes also generates a self-receive signal, which is an attenuated repetition of the outgoing synchronization signal. The system 200 generates this self-receive signal by internally reflecting an attenuated repetition of the outgoing synchronization signal (e.g., via an impedance mismatch at the interface between the passive coupling device 240 and the antenna), which is then received by the same node that transmitted the synchronization signal (e.g., via the receive port 246 of the passive coupling device 240). Because the system 200 reflects the self-receive signal along the same receive chain that the synchronization at which the signal is received, the system 200 ensures that the self-receive signal are characterized by a similar time delay (e.g., within than one nanosecond) relative to the time delay of the synchronization signal due to reception at the system 200 and a similar phase shift (e.g., a few degrees) relative to the phase shift of the synchronization signal due to reception at the system 200. Therefore, the TOA of the self-receive signal and the carrier phase of the self-receive signal are offset by a substantially similar time delay and a substantially similar phase shift to those incurred by the synchronization signal upon reception by the system 200.

Thus, the TOA of the self-receive signal acts as a time-of-departure of the synchronization signal approximately offset by the time delay of the receive chain of the transmitting node, while the carrier phase of the self-receive signal acts as a "carrier-phase-of-departure" for the synchronization signal approximately offset by the phase shift of the receive chain of the transmitting node.

Therefore, while executing this synchronization protocol, each node in the pair of nodes has recorded a TOA and a carrier phase for one self-receive signal and for one synchronization signal received from the opposite node resulting in four TOA values and four carrier phase values. The system executing this time synchronization protocol can then solve a system of equations based on the four TOA values, algebraically canceling out the time delays of the receive chains of each node, in order to calculate the time bias and propagation time between the pair of nodes. The system executing this time synchronization protocol can then further refine this time bias and propagation time calculation utilizing the four carrier phase values generated by the pair of nodes. Therefore, the system 200 can enable characterization of the time bias between a pair of nodes and the propagation time between the pair of nodes.

More specifically, a first node and a second node in the pair of nodes and/or a remote system communicating with these nodes can be configured to execute a two-way time synchronization protocol by, at the first node: transmitting a first synchronization signal; and generating a first self-receive signal based on the first synchronization signal. Then the second node can: transmit a second synchronization signal; and generate a second self-receive signal based on the second synchronization signal. Once the first node and the second node have each transmitted a synchronization signal and generated a self-receive signal, the first node can: calculate a first time-of-arrival of the first self-receive signal; and calculate a second time-of-arrival of the second synchronization signal. The second node can then: calculate a third time-of-arrival of the second self-receive signal; and calculate a fourth time-of-arrival of the first synchronization signal. Then a system in communication with the first node and the second node or one of the nodes themselves can calculate a time bias and a propagation delay between the first node and the second node based on the first time-of-arrival, the second time-of-arrival, the third time-of-arrival, and the fourth time-of-arrival.

2.3 Hardware

In one implementation, the system 200 is included in an RF transceiver and includes RF hardware such as a superheterodyne radio architecture, or other RF front-end architecture such as direct conversion, direct-IF conversion, or zero-IF conversion, and a transmit-receive antenna 230 shown in FIG. 4. In this implementation, the system 200 includes a receive chain and a transmit chain. The receive chain includes a pipeline of hardware components that process signals received from the receive 246. The transmit chain includes a pipeline of hardware components that process transmission signals generated by the FPGA or DSP and feed them into the transmit port 244. In one implementation, the FPGA or DSP of the system 200 is configured to generate complex digital signals and output the generated signals to a DAC. The complex components of the digital signals represent the in-phase and quadrature portions (i.e. I/Q) of the analog signal to be generated by the DAC. Additionally, the FPGA or DSP of the node receives digital signals from the antenna 230 of the node via an ADC 222. However, the system 200 can be included in a transceiver in media other than RF. For example, the system 200 can be integrated into an optical transceiver or a sonic transceiver (e.g., sonar).

The system 200 includes a passive coupling device 240, which couples the transmit chain and the receive chain to the antenna port 242 or another output port. The passive coupling device 240 can include a directional coupler, a power divider, a circulator, or any other device capable of coupling transmission lines (e.g., RF, optical, sonic, or for any other medium) to an antenna 230 or output port.

The system 200 includes an impedance matching network 250 coupled to the antenna port 242 of the passive coupling device 240. The impedance matching network 250 maintains a precise impedance mismatch and therefore a precise reflection coefficient at the antenna port 242 interface and, in combination with the passive coupling device 240, reflects transmitted signals from the transmit port 244 to the receive port 246 of the passive coupling device 240.

In an alternate implementation, the system 200 can integrate with a wired communication system. In this implementation, the system 200 can include an I/O port (instead of an antenna port 242) and/or appropriate interface converters for communicating over any wired medium (e.g. ethernet, fiber optic, etc.) instead of an antenna 230.

The system 200 can also include a clock, such as a crystal oscillator clock or an atomic clock, which can be responsible for time-keeping functions at the system 200. In one example, the clock is a quartz crystal oscillator with an AT cut and a clock frequency of ten megahertz. However, the system 200 can include a crystal oscillator of any frequency or cut assuming the aforementioned constraints are met. Additionally, the system 200 can include oven-controlled crystal oscillators.

In one implementation, the system 200 can include a software-defined radio architecture performing the function of any of the hardware elements described above.

2.3.1 Passive Coupling Device

Figure 5:
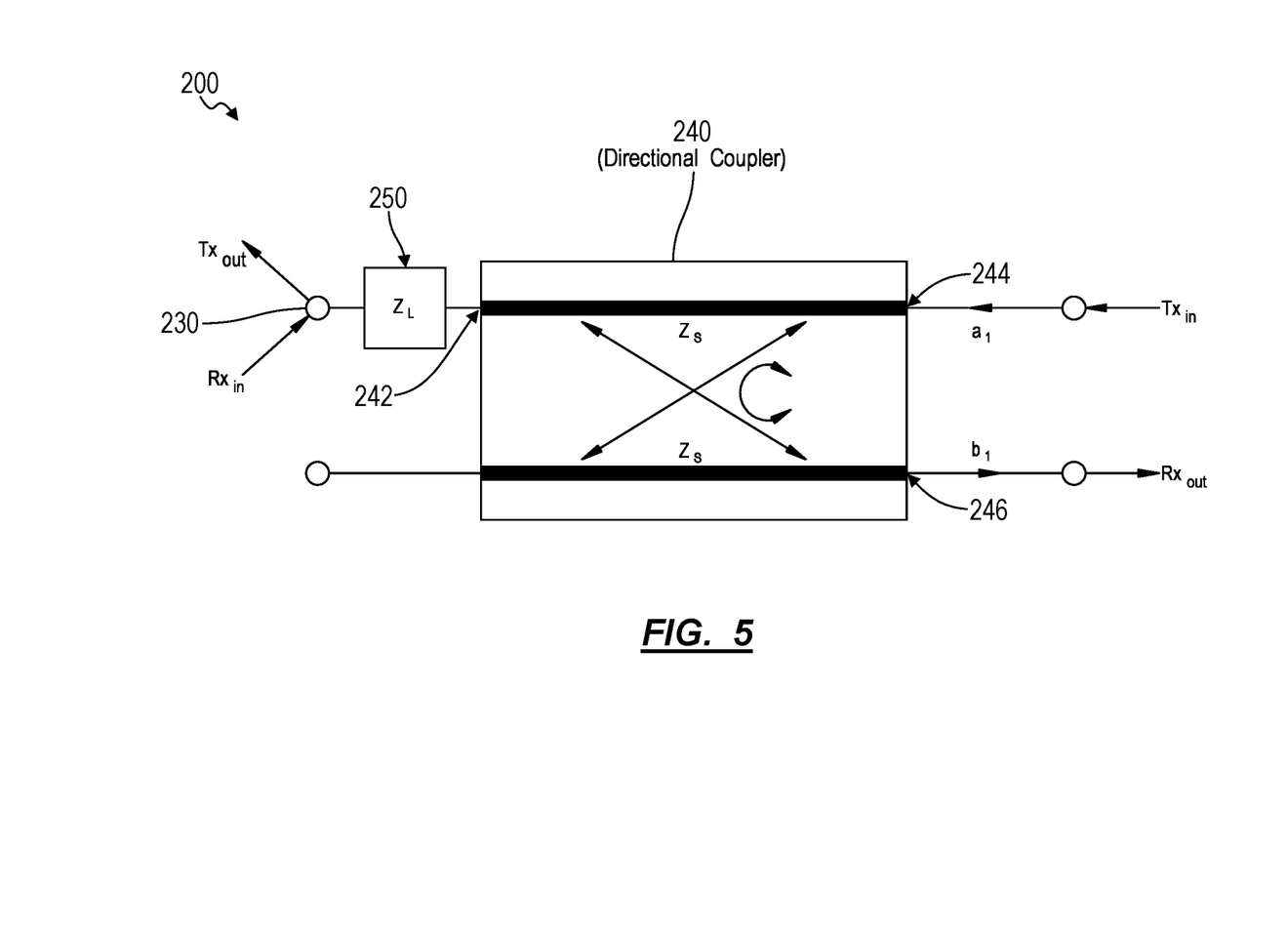
FIG. 5 is a schematic representation of the second system.

As shown in FIG. 5, the system 200 includes an assembly of the passive coupling device 240 and the impedance matching network 250, which together generate a self-receive signal. The passive coupling device 240 is connected via three of its ports to the transmit port 244, the receive port 246, and the antenna 230 (or output) port. In addition to routing the self-receive signal from the transmit port 244 to the receive port 246, the passive coupling device 240 enables the transceiver to use one antenna 230 (or I/O port) for both transmitting and receiving functions. Therefore, the passive coupling device 240 also functions to transmit signals from the transmit port 244 to the antenna port 242, and from the antenna port 242 to the receive port 246. Thus, the system 200 can include any device that may satisfy the above constraints, such as a directional coupler, a power divider, a circulator, or any other transmission line coupling device.

The passive coupling device 240 is characterized by a characteristic impedance, which, in a standard RF implementation, may be 50Ω or 75Ω.

In one implementation, the passive coupling device 240 is a directional coupler. A typical directional coupler has four ports referred to as the input port, the transmitted port, the coupled port, and the isolated port, wherein the input port and the transmitted port are connected directly via a first transmission line and the isolated port and the coupled port are connected by a second transmission line loosely coupled to the first transmission line. Thus, RF power transmitted in the first transmission line from the input port to the transmitted port is also transferred to the coupled port. However, RF power is not transmitted from the isolated port, which is terminated with the characteristic impedance of the transmission line and dissipates RF power in a resistor with corresponding impedance value. When integrated with the system 200, the input port of the directional coupler can function as the antenna port 242 and can be connected to the matching network and antenna 230. The transmitted port can function as the transmit port 244 and the coupled port can function as the receive port 246. The isolated port in this implementation can be terminated with the characteristic impedance of the directional coupler. Thus, any signals received at the antenna 230 are coupled to the receive port 246 and any self-receive signals at the antenna port 242 are back-coupled to the receive port 246. More specifically, the system 200 can include a directional coupler, as the passive coupling device 240, the directional coupler including an input port electromagnetically coupled to the antenna 230; a transmitted port electromagnetically coupled to the transmit chain; and a coupled port electromagnetically coupled to the receive chain.

Because the directional coupler does not couple signals at full power, any signal coupled between the antenna port 242 and the receive port 246 may be attenuated according to the coupling factor of the directional coupler. As such, in implementations where the transceiver is capable of increased transmit power, the system 200 can include a directional coupler where the receive port 246 is located on the same transmission line as the antenna port 242 and the transmit port 244 is located on the coupled transmission line. Thus, the power of the transmitted signal is attenuated according to the coupling factor of the directional coupler before being transmitted and/or reflected at the antenna port 242.

Additionally, the system 200 can include a directional coupler with multiple coupling sections, wherein each coupling section is optimized for a different frequency band. The coupling factor of each coupling section can also be adjusted to modify the gain of the coupled signal at a particular frequency band.

In another implementation, the system 200 includes a power divider acting as the passive coupling device 240. In this implementation, the transmit port 244 and the receive port 246 are located at each of the divided ports of the power divider while the antenna port 242 is located at the input port of the power divider. Because the power divider splits power more evenly between the transmit port 244 and the receive port 246, the self-receive signal can be received with a potentially higher power in this implementation. More specifically, the system 200 can include a power divider as the passive coupling device 240, the power divider including: an input port electromagnetically coupled to the antenna 230; a transmitted port electromagnetically coupled to the transmit chain; and a coupled port electromagnetically coupled to the receive chain.

In yet another implementation, the system 200 includes a circulator acting as the passive coupling device 240. The circulator can include the transmit port 244 at a first port, the antenna port 242 at a second port, and the receive port 246 at the third port. The circulator can be further configured to deliver power directly from the transmit port 244 to the antenna port 242, and from the antenna port 242 to the receive port 246. Additionally, any reflection from the antenna port 242 interface will reflect from the antenna port 242 to the receive port 246. More specifically, the system 200 can include a circulator as the passive coupling device 240, the circulator including: a first circulator port electromagnetically coupled to the antenna 230 and configured to transmit signals to a second circulator port; the second circulator port electromagnetically coupled to the receive chain and configured to transmit signals to a third circulator port; and the third circulator port electromagnetically coupled to the transmit chain and configured to transmit signals to the first circulator port.

2.3.2 Impedance Matching Network

The system 200 includes an impedance matching network 250 located at the antenna port 242 of the passive coupling device 240. The impedance matching network 250 is designed such that it transforms the impedance of the antenna 230, not to match the characteristic impedance of the passive coupling device 240, but instead to match a specific load impedance that effects a particular reflection coefficient at the interface between the passive coupling device 240 and the antenna 230 (i.e. the antenna port 242 interface). More specifically, the system 200 includes an impedance matching network 250 configured to transform the antenna impedance of the antenna 230 to a load impedance, the load impedance and the characteristic impedance defining a reflection coefficient sufficient to reflect signals transmitted from the transmit port 244 and at the transmit voltage toward the receive port 246 at a receive voltage between the input noise floor and the input saturation voltage.

The impedance matching network 250 can be implemented in a number of configurations depending on the particular design of the system 200. For example, the system 200 can include L, T, and/or Pi impedance matching networks 250. Alternatively, the system 200 can include cascaded L networks to increase the effective bandwidth of the matching network.

The system 200 can also include additional impedance matching networks 250 at the transmit port 244 and the receive port 246 of the passive coupling device 240 to improve power transfer of signals between the transmit port 244 and the passive coupling device 240 and between the passive coupling device 240 and the receive port 246. These secondary impedance matching networks 250 are matched to the characteristic impedance of the passive coupling device 240.

2.3.2.1 Mismatched Impedance Calculation

As described above, the system 200 includes an impedance matching network 250 that matches a specific load impedance that effects a particular reflection coefficient at the antenna port 242 interface. Thus, the matching impedance value for the impedance matching network 250 is a function of the reflection coefficient, which can be determined based on the transmit voltage of the system 200, the noise floor of the ADC 222 included in the receive chain of the system 200, and the saturation voltage of the ADC 222. More specifically, the system 200 can include a impedance matching network 250 that shifts the antenna impedance to a load impedance equal to a function of the transmit voltage, a desired signal voltage between the input noise floor and the input saturation voltage, a coupling factor of the passive coupling device 140 and proportional to the characteristic impedance of the passive coupling device 140.

In one implementation, the system 200 includes an impedance matching network 250 with an impedance value such that the self-receive signal is received at the ADC 222 at an average power that is sufficiently above the noise floor of the ADC 222 to achieve a minimum operating SNR while sufficiently below the saturation voltage of the ADC 222 to maintain linearity in the digitized received signals of the ADC 222. Alternatively, the system 200 can utilize any received power between the noise floor and the saturation voltage of the ADC 222. In implementations of the system 200 with a variable impedance matching network 250, the system 200 can also maximize the overall transmitted power to increase the signal power levels with respect to interference in the operating frequency bands to improve reception range and reliability of the system 200. In this case, the system 200 can include a matched impedance to the transmission line characteristic impedance given physical tolerances in matching network component values and parameters, so as to minimize the back-reflected power from the antenna 230 or port to avoid saturation of the ADC 222 or damage to other RF components. The desired signal voltage at the ADC 222 can be expressed as $b_1$ while the transmit voltage can be expressed as $a_1$. Additionally, the coupling factor of the passive coupling device 240 is represented as C, which represents the attenuation of the signal as it is back-coupled to the receive port 246. Thus, the reflection coefficient is given by the following equation:

$$\Gamma = \frac{b_1}{a_1 C}$$

In order to effect the desired r, the impedance mismatch between the characteristic impedance of the passive coupling device 240 and the effective impedance of the antenna 230 is given by:

$$\Gamma = \frac{Z_L - Z_S}{Z_L + Z_S}$$

where $Z_L$ is the particular load impedance of the antenna 230 and $Z_S$ is the characteristic impedance of the passive coupling device 240. Thus:

$$\frac{b_1}{a_1 C} = \frac{Z_L - Z_S}{Z_L + Z_S}$$

Therefore, solving for $Z_L$ gives $$Z_L = \frac{\left(1 + \frac{b_1}{a_1 C}\right)}{\left(1 - \frac{b_1}{a_1 C}\right)} Z_s$$

Thus, given values for $$\frac{b_1}{a_1 C}$$

and $Z_s$, the impedance value of the impedance matching network 250 can be calculated. For example, if $$\frac{b_1}{a_1 C} = 0.01 \text{ and } Z_s = 50\Omega, \text{ then } Z_L = 51.01\Omega$$

(assuming $Z_s$ and $Z_L$ are purely resistive).

The system 200 includes a matching network that transforms the impedance value of the antenna 230 to the value of $Z_L$ instead of the value of $Z_s$. As a result, the system 200 includes an antenna 230 that is intentionally impedance-mismatched to the characteristic impedance of the passive coupling device 240.

However, small variations of $Z_L$ can cause large variations in the reflection coefficient. For example, a change from 51Ω to 52Ω can double the reflection coefficient when $Z_s$=50Ω. Thus, the system 200 can include more precise impedance matching networks 250 than may otherwise be included in a standard transceiver.

2.3.2.2 Cascaded L Matching Networks

In one implementation, the system 200 includes a cascaded L matching network to improve the bandwidth of the impedance matching network 250. The cascaded L matching network can include an arbitrarily large number of L matching networks, which can improve bandwidth to the impedance matching network 250 at the expense of greater insertion loss for the impedance matching network 250.

2.3.2.3 Switchable Wideband Matching Networks

In one implementation, the system 200 includes a switchable wideband matching network to improve the bandwidth of the impedance matching network 250. More specifically, the system 200 can include: a switchable wideband matching network defining a set of impedance matching networks 250, each impedance matching network 250 in the set of impedance matching networks 250 configured to maintain the reflection coefficient for a frequency band of signals generated by the signal generator 210; and a controller configured to actuate a switch in the switchable wideband matching network between the set of impedance matching networks 250, where the controller is configured to actuate a switch in the switchable wideband matching network between the set of impedance matching networks 250 based on a frequency band of signals generated by the signal generator 210.

The switchable wideband matching network includes a physical switch controlled by the FPGA in the transceiver that can switch between a set of impedance matching networks 250. Depending on the frequency being transmitted at the transmit port 244, the FPGA can switch to an impedance matching network 250 in the set of impedance matching networks 250 that is designed according to the particular frequency being transmitted. Thus, the system 200 can generate self-receive signals over a significantly larger bandwidth than implementations including only a single impedance matching network 250.

In an alternative implementation, the system 200 can include impedance matching networks 250 characterized by different impedance values such that the system 200 can switch impedance matching networks 250 in order to alter the reflection coefficient and therefore the power of the self-receive signal in response to changes in the signal-to-noise-ratio (hereinafter "SNR") at the ADC 222 or in the transmit power at the signal generator 210. Thus, in this implementation, the system 200 can adjust the power of the self-receive signal in response to changing conditions in order to maintain a received power of the self-receive signal with a high SNR without saturating the ADC 222. More specifically, the system 200 can include a controller configured to actuate a switch in the switchable wideband matching network between the set of impedance matching networks 250 based on an SNR of reflected signals received at the ADC 222.

2.3.2.4 Multiplexed Matching Networks

In one implementation, the system 200 includes a multiplexed impedance matching network 250. More specifically, the system 200 includes: a multiplexed matching network defining a set of impedance matching networks 250, each impedance matching network 250 in the set of impedance matching networks 250 configured to maintain the reflection coefficient for a frequency band of signals generated by the signal generator 210; and a controller configured to select a matching network in the set of impedance matching networks 250 via a multiplexer in the multiplexed matching network.

The multiplexed impedance matching network 250 includes an analog frequency demultiplexer coupled to the antenna port 242 of the passive coupling device 240. On each demultiplexed channel of the demultiplexer, the system 200 can include a distinct matching network designed for the frequency corresponding to the demultiplexed channel. The system 200 further includes an analog frequency multiplexer that recombines each of the channels, which is coupled to the antenna 230. Thus, the multiplexed impedance matching network 250 can present a distinct impedance matching network 250 for each frequency transmitted by the system 200.

2.3.2.5 Lossy Impedance Matching

In one implementation, the system 200 can include lossy impedance matching networks 250 including resistors, as resistive impedance matching networks 250 have better wideband performance than inductor/capacitor based matching networks. In this implementation, the system 200 can include additional amplifiers to counteract the power loss incurred by the resistive impedance matching networks 250.

2.3.2.6 Reactance Cancellation

In one implementation, the system 200 can also include impedance matching networks 250 that cancel the reactance of the antenna 230 but maintain the aforementioned impedance mismatch between the passive coupling device 240 and the antenna 230. By cancelling the reactance of the antenna 230 while maintaining an impedance mismatch between the antenna 230 and the passive coupling device 240, the system 200 ensures that the self-receive signal is well-received at the ADC 222 with the same phase offset as a signal received via the antenna 230.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system for generating reference signals comprising:
a signal generator configured to generate a first signal;
an antenna:
   coupled to the signal generator; and
   configured to:
      broadcast the first signal; and
      receive a second signal;
a first signal processor;
a second signal processor;
a first coupling device:
   interposed between the signal generator and the first signal processor; and
   configured to relay a first reference signal, comprising a first representation of the first signal and characterized by a first phase delay and a first propagation delay, from the signal generator to the first signal processor; and
a second coupling device:
   interposed between the antenna and the second signal processor; and
   configured to relay a second reference signal, comprising a second representation of the second signal and characterized by a second phase delay and a second propagation delay approximating the first propagation delay, from the antenna to the second signal processor.

2. The system of claim 1:
wherein the first coupling device comprises:
   a first port coupled to the signal generator; and
   a second port coupled to the first signal processor; and
further comprising:
   an attenuator:
      interposed between the second port and the first signal processor; and
      configured to impart a first group delay to the first reference signal.

3. The system of claim 2:
wherein the second coupling device comprises:
   comprising a third port coupled to the antenna; and
   comprising a fourth port coupled to the second signal processor; and
further comprising:
   an amplifier:
      interposed between the fourth port and the second signal processor; and
      configured to impart a second group delay to the second reference signal, the second group delay approximating the first group delay.

4. The system of claim 1:
further comprising a clock; and
wherein the first signal processor is configured to, in response to receiving the first reference signal and based on the first propagation delay, calculate a first time-of-arrival of the first reference signal at the first signal processor according to the clock, the first time-of-arrival approximating a broadcast time of the first signal from the antenna.

5. The system of claim 1:
further comprising a clock; and
wherein the second signal processor is configured to calculate a second time-of-arrival of the second reference signal at the second signal processor according to the clock based on the second propagation delay in response to receiving the second reference signal, the second time-of-arrival approximating a receive time of reception of the second signal at the antenna.

6. The system of claim 1:
wherein the first signal processor comprises a first analog-to-digital converter configured to sample the first reference signal; and
wherein the second signal processor comprises a second analog-to-digital converter configured to sample the second reference signal.

7. The system of claim 1, further comprising:
a self-receive chain comprising the first coupling device and characterized by a first path length defining the first propagation delay; and
a receive chain comprising the second coupling device and characterized by a second path length defining the second propagation delay.

8. A system comprising:
a signal generator configured to generate a first signal;
an antenna:
  coupled to the signal generator; and
  configured to:
    broadcast the first signal; and
    receive a second signal;
a first signal processor;
a second signal processor;
a self-receive chain:
  characterized by a first path length defining a first propagation delay;
  coupling the signal generator and the first signal processor; and
  configured to relay a first reference signal, characterized by the first propagation delay and a first phase delay and comprising a first representation of the first signal, from the signal generator to the first signal processor; and
a receive chain:
  characterized by a second path length approximating the first path length and defining a second propagation delay;
  coupling the antenna and the second signal processor; and
  configured to relay a second reference signal, characterized by the second propagation delay and a second phase delay and comprising a second representation of the second signal, from the antenna to the second signal processor.

9. The system of claim 8:
wherein the receive chain is further configured to relay the second reference signal characterized by the second phase delay approximating the first phase delay.

10. The system of claim 8, further comprising a first coupling device:
configured to:
  relay the first reference signal from the signal generator to the first signal processor; and
  relay the first signal from the signal generator to the antenna;
comprising:
  a first port coupled to the signal generator;
  a second port; and
  a third port coupled to the first signal processor; and
characterized by a first phase balance between the second port and the third port.

11. The system of claim 10, further comprising an attenuator:
interposed between the third port and the first signal processor; and
configured to impart a first group delay to the first reference signal.

12. The system of claim 10, further comprising a power amplifier:
interposed between the first signal processor and the first port; and
configured to amplify the first reference signal.

13. The system of claim 10:
further comprising a second coupling device:
  configured to:
    relay the second reference signal from the antenna to the second signal processor;
  comprising:
    a fourth port coupled to the antenna;
    a fifth port coupled to the second port; and
    a sixth port coupled to the second signal processor; and
  characterized by a second phase balance between the fifth port and the sixth port, the second phase balance approximating the first phase balance; and
a low-noise amplifier:
  interposed between the sixth port and the second signal processor; and
  configured to impart a second group delay to the second reference signal, the second group delay approximating the first group delay.

14. The system of claim 8:
further comprising a clock; and
wherein the first signal processor is configured to, in response to receiving the first reference signal, calculate a first time-of-arrival of the first reference signal at the first signal processor according to the clock, the first time-of-arrival approximating a broadcast time of the first signal from the antenna.

15. The system of claim 8, wherein the first signal processor is configured to calculate a time-of-arrival of the first reference signal at the first signal processor, the time-of-arrival approximating a time-of-departure of the first signal from the antenna based on the first propagation delay.

16. A system comprising:
a signal generator configured to generate a first signal;
an antenna:
  coupled to the signal generator;
  configured to:
    broadcast the first signal; and
    receive a second signal;
a first signal processor;
a self-receive chain:
  characterized by a first path length defining a first propagation delay;
  coupling the signal generator and the first signal processor; and
  configured to relay a first reference signal, characterized by the first propagation delay and a first phase delay and comprising a first representation of the first signal, from the signal generator to the first signal processor; and a receive chain:
  characterized by a second path length defining a second propagation delay approximating the first propagation delay;
  coupling the antenna and the first signal processor; and
  configured to relay a second reference signal, characterized by the second propagation delay and a second phase delay and comprising a second representation of the second signal, from the antenna to the first signal processor.

17. The system of claim 16:
further comprising a multiplexer comprising:
  a first reference signal port;
  a second reference signal port; and
  an output port coupled to the first signal processor;
wherein the self-receive chain comprises the first reference signal port; and
wherein the receive chain comprises the second reference signal port.

18. The system of claim 17:
further comprising a controller:
  coupled to the multiplexer; and
  configured to output a first controller signal and a second controller signal; and
wherein the multiplexer is configured to:
  at a first time:
    access the first controller signal; and
    based on the first controller signal, route the first reference signal, via the first reference signal port, to the first signal processor; and
  at a second time:
    access the second controller signal; and
    based on the second controller signal, route the second reference signal, via the second reference signal port, to the first signal processor.

19. The system of claim 16, further comprising a power combiner configured to:
  merge the self-receive chain and the receive chain; and
  concurrently relay the first reference signal and the second reference signal to the first signal processor.

20. The system of claim 16:
wherein the first signal processor is configured to calculate a time-of-arrival of the first reference signal at the first signal processor, the time of arrival a time-of-departure of the first signal from the antenna based on the first propagation delay.

* * * * *